United States Patent [19]
Levesque et al.

[11] Patent Number: 6,076,407
[45] Date of Patent: Jun. 20, 2000

[54] PIPE INSPECTION PROBE

[75] Inventors: Michael Paul Levesque; John Paul Sheppard, II, both of Lynchburg; Matthew Wayne Ales, Amherst, all of Va.

[73] Assignee: Framatome Technologies, Inc., Lynchburg, Va.

[21] Appl. No.: 09/079,578

[22] Filed: May 15, 1998

[51] Int. Cl.[7] .................................................. G01N 29/24
[52] U.S. Cl. ............................ 73/623; 73/866.5; 324/220
[58] Field of Search .................... 73/866.5, 623, 73/40.5 R, 40.5 A, 865.8; 324/220, 221

[56] References Cited

U.S. PATENT DOCUMENTS

| | | | |
|---|---|---|---|
| 3,862,578 | 1/1975 | Schlüter | 73/866.5 |
| 4,304,134 | 12/1981 | Rouse et al. | 324/220 |
| 4,581,927 | 4/1986 | Johnson | 73/152.36 |
| 4,820,982 | 4/1989 | Aubert | 324/300 |
| 4,843,896 | 7/1989 | Napeloni et al. | 73/866.5 |
| 5,105,881 | 4/1992 | Thoms et al. | 73/784 |
| 5,195,392 | 3/1993 | Moore et al. | 73/866.5 |
| 5,520,245 | 5/1996 | Estes | 73/152.56 |
| 5,565,633 | 10/1996 | Wernicke | 73/866.5 |
| 5,760,306 | 6/1998 | Wyatt, III et al. | 73/623 |

*Primary Examiner*—Hezron Williams
*Assistant Examiner*—Nashmiya Fayyaz
*Attorney, Agent, or Firm*—Rhodes & Mason, PLLC

[57] ABSTRACT

A probe for inspecting the inside of a large diameter, substantially vertical, limited access pipe. The probe includes an elongated probe housing having a series of flexible joint along its length to permit the probe to be positioned within the pipe. A plurality of radially extendable guide arms are attached to the lower end of the probe housing for positioning the probe within the pipe and, in the preferred embodiment, a stabilizer weight is attached to the elongated housing adjacent to the guide arms for preventing unstable movement of the probe much like a tail on a kite. In the preferred embodiment, the probe further includes a rotational drive for rotating the plurality of radially extendable guide arms with respect to the elongated housing. In addition, sensors are located on the ends of each guide arm to permit the inside surface of the pipe to be more completely inspected for defects. Also, an axial drive moves the probe along the length of the pipe and is controlled by an output from the drive for rotating the plurality of radially extendable guide arms with respect to the elongated housing.

34 Claims, 5 Drawing Sheets

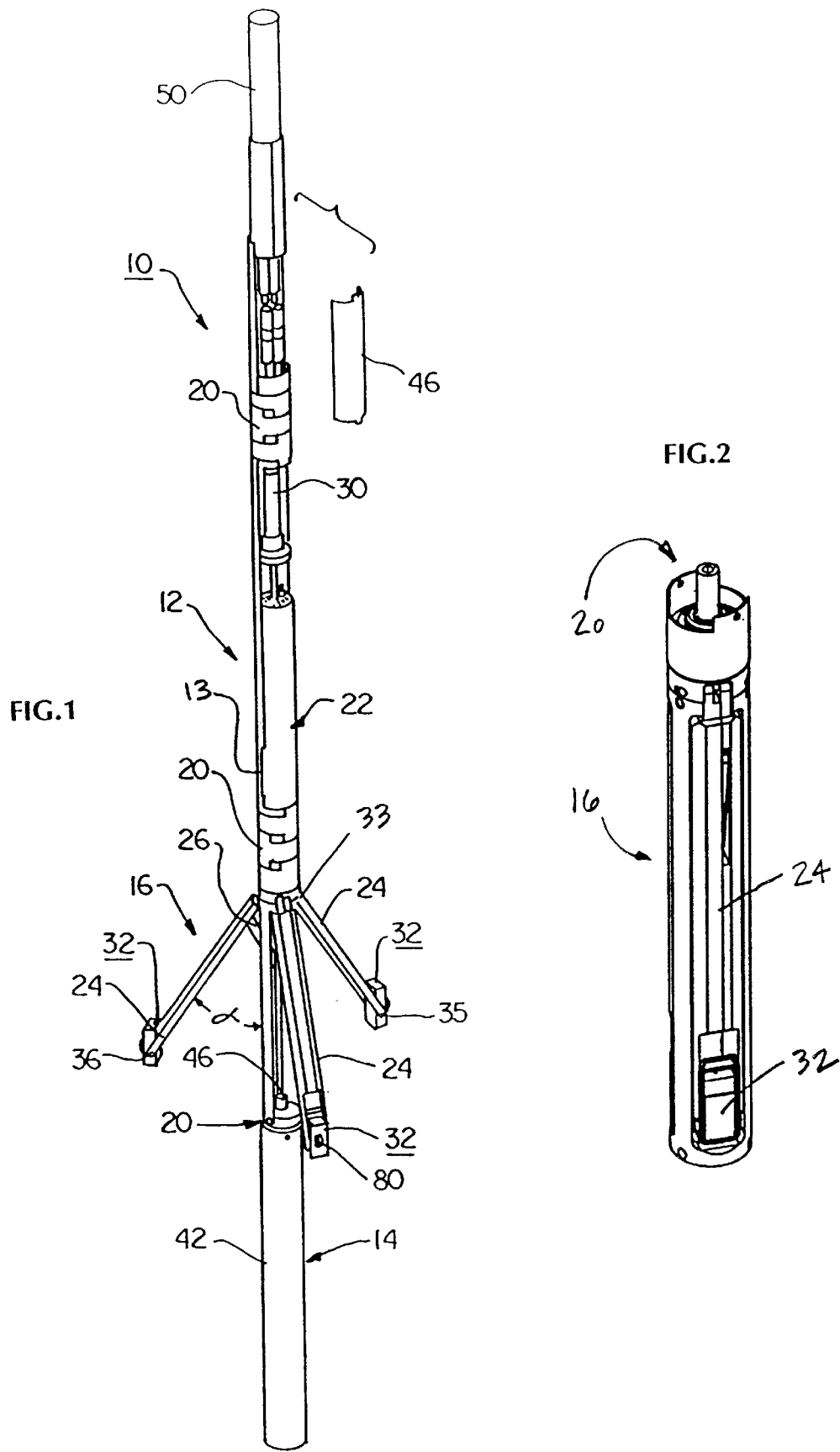

PIPE INSPECTION PROBE

BACKGROUND OF THE INVENTION

(1) Field of the Invention

The present invention relates generally to an apparatus for inspecting the interior of generally vertical conduits or piping and, more particularly, to an apparatus for detecting and determining both the axial and angular positions of detected defects in the variable diameter jet pump diffusers such as found in a boiling water (BWR) nuclear reactors.

(2) Description of the Prior Art

Coolant piping in a BWR must be periodically inspected to detect cracking due to either intergranular Stress Corrosion Cracking (IGSCC) or fatigue in the tubing walls, so that these areas can be repaired to prevent leakage. Usually detection is performed externally since there was no way to insert an inspection probe into the jet pump diffuser assembly consisting of the jet pump mixers, diffuser and adapters. This is because the access opening to the internal tubing is limited while the inside diameter of the piping may vary over its length from between about 3 to 22 inches. However, because of supports and other attachments, not every portion of the piping can be inspected externally.

Probes have been developed to detect and located defects inside the much smaller steam generator tubing which has an inside diameter of about ¾ inch. These probes may include a rotatable probe head positioned at the end of a tubular carrier through which electrical wiring connects the drive means and detector of the probe head to an external power source and controls. The probe head includes a detector, e.g., an ultrasonic detector, an eddy current detector, or both, which measures changes in wall conditions.

The axial position of the wall defect can be determined by measuring the distance that the probe head has been inserted into the tubing. In addition, encoders have been used to determine the angular position of the defect which is helpful in properly correcting the defect. One example of such a probe for steam generator tubing is disclosed in U.S. Pat. No. 5,760,306 (to be issued Jun. 2, 1998), issued to Wyatt, III et al., which is hereby incorporated by reference in its entirety. However these probes could not be used for the much larger and variable diameter jet pump diffuser assembly piping which varies between about 3 and 22 inches over its length.

Thus, there remains a need for a new and improved apparatus for detecting and determining both the axial and angular positions of detected defects in the inside of a pipe while, at the same time, is able to conform to large, variable diameter jet pump diffusers such as found in a BWR nuclear reactors.

SUMMARY OF THE INVENTION

The present invention is directed to a probe for inspecting the inside of a large diameter, substantially vertical, limited access pipe. The probe includes an elongated probe housing having a series of flexible joint along its length to permit the probe to be positioned within the pipe. Each of the flexible joints permits axially bending of about ±5° each to permit the probe to turn into a limited access inspection port.

A plurality of radially extendable guide arms are attached to the lower end of the probe housing for positioning the probe within the pipe and, in the preferred embodiment, a stabilizer weight is attached to the elongated housing adjacent to the guide arms for preventing unstable movement of the probe. The center of gravity of the weight is below the plane determined by the contact points between the outer ends of the guide arms and the pipe wall thereby maintaining axial alignment of the probe and causing the ends of the guide arms to move in a true helical pattern as the probe moves through the pipe. In addition, the stabilizer weight is attached to the elongated housing by a flexible joint to further aid in access to difficult to reach inspection ports.

In the preferred embodiment, the probe further includes a rotational drive for rotating the plurality of radially extendable guide arms with respect to the elongated housing. In addition, sensors may be located on the ends of each guide arm to permit the inside surface of the pipe to be more completely inspected for defects. Also, an axial drive moves the probe along the length of the pipe and is controlled by an output from the drive for rotating the plurality of radially extendable guide arms with respect to the elongated housing.

Accordingly, one aspect of the present invention is to provide a probe for inspecting the inside of a large diameter, substantially vertical pipe. The probe including: (a) an elongated probe housing adapted to be positioned within the pipe; and (b) a plurality of radially extendable guide arms attached to the lower end of the probe housing for positioning the probe within the pipe.

Another aspect of the present invention is to provide a probe for inspecting the inside of a large diameter, substantially vertical, limited access pipe. The probe includes: (a) an elongated probe housing having at least one flexible joint along its length to permit the probe to be positioned within the pipe; and (b) a plurality of radially extendable guide arms attached to the lower end of the probe housing for positioning the probe within the pipe.

Still another aspect of the present invention is to provide a probe for inspecting the inside of a large diameter, substantially vertical, limited access pipe. The probe includes: (a) an elongated probe housing having at least one flexible joint along its length to permit the probe to be positioned within the pipe; (b) a plurality of radially extendable guide arms attached to the lower end of the probe housing for positioning the probe within the pipe; and (c) a stabilizer weight attached to the elongated housing adjacent to the guide arms for preventing unstable movement of the probe.

These and other aspects of the present invention will become apparent to those skilled in the art after a reading of the following description of the preferred embodiment when considered with the drawings.

BRIEF DESCRIPTION OF THE DRAWINGS

FIG. 1 is a perspective view of a probe constructed according to the present invention having the guide arms in a radially extended position and having portions of the outer housing cut-away for detail into the interior of the invention;

FIG. 2 is a cut-away view of the guide arms of the probe illustrating the guide arms in a closed retracted position;

DESCRIPTION OF THE PREFERRED EMBODIMENTS

Figure 3:
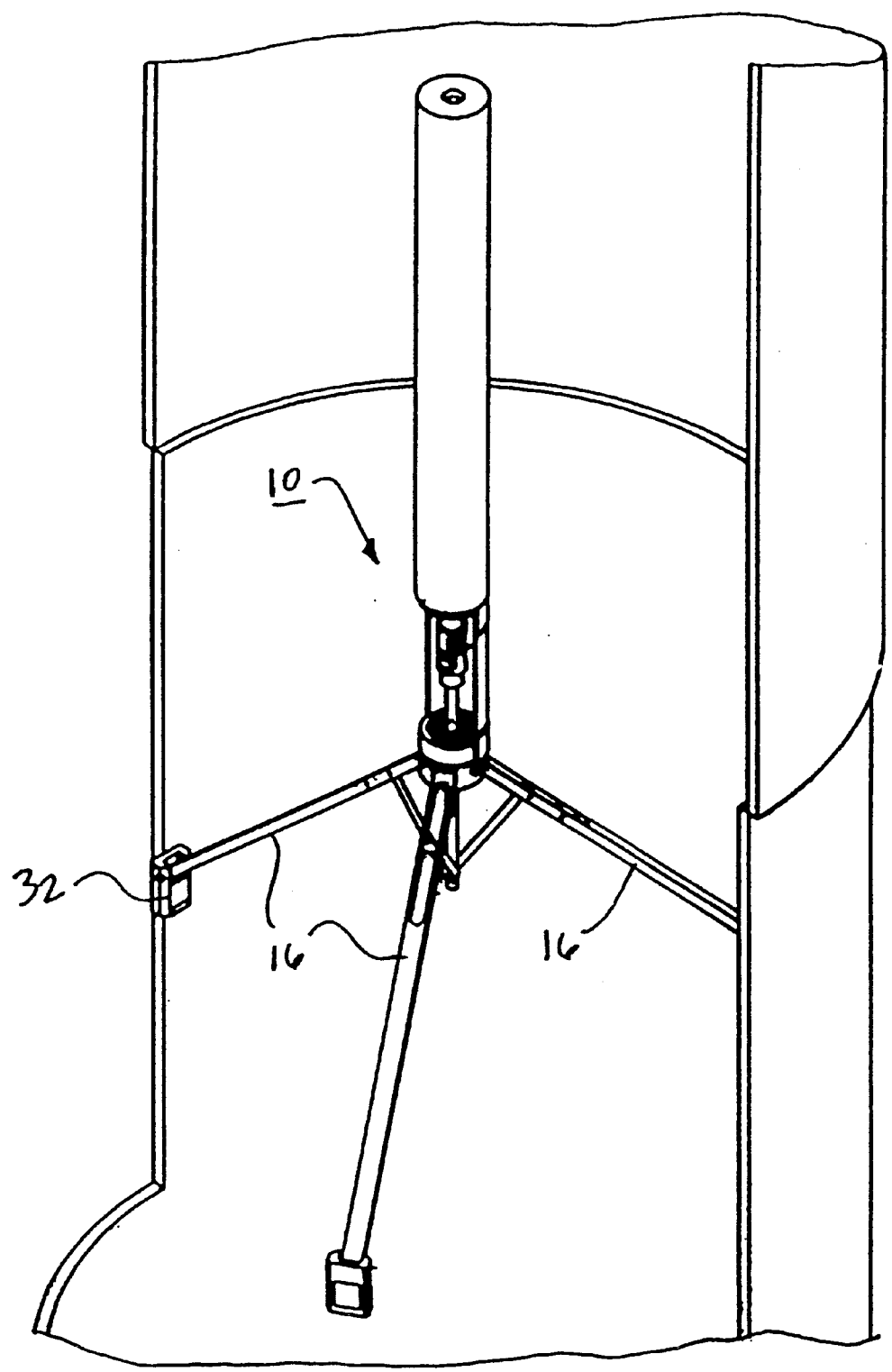
FIG. 3 is a cut-away view of the probe having the guide arms radially extended along the inside diameter of a pipe.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Referring now to the drawings in general and FIG. 1 in particular, it will be understood that the illustrations are for the purpose of describing a preferred embodiment of the invention and are not intended to limit the invention thereto. The invention is a remotely controlled tool used for the ultrasonic inspection of the welds in the jet pump diffusers of a boiling water reactor. As best seen in FIG. 1, a probe for inspecting a vertically oriented, variable inside diameter pipe, generally designated 10, is shown constructed according to the present invention. The probe 10 includes a probe head 12 having an elongated housing 13 and a plurality of guide arms 16. The elongated housing 13 includes a plurality of flexible joints 20 spaced along the length to allow the probe to be inserted and moved through various pipe configurations. A rotational drive motor 22 rotates the guide arms 16 along the inside diameter of the pipe and an axial drive motor 44 located upstream of the probe provides for movement of the probe along the pipe length. In the preferred embodiment, the probe 10 further includes a weight 14 attached to the lower end of the probe head 12 for maintaining the vertical orientation of the probe in the interior of the pipe.

The elongated housing 13 functions to protect the drive elements from damage during use. In a preferred embodiment, the housing 13 is constructed of high strength aluminum or stainless steel. The housing 13 may include removable sections 46 to provide access to specific interior sections of the probe head and are preferably placed over areas that may require repair or calibration.

Figure 5:
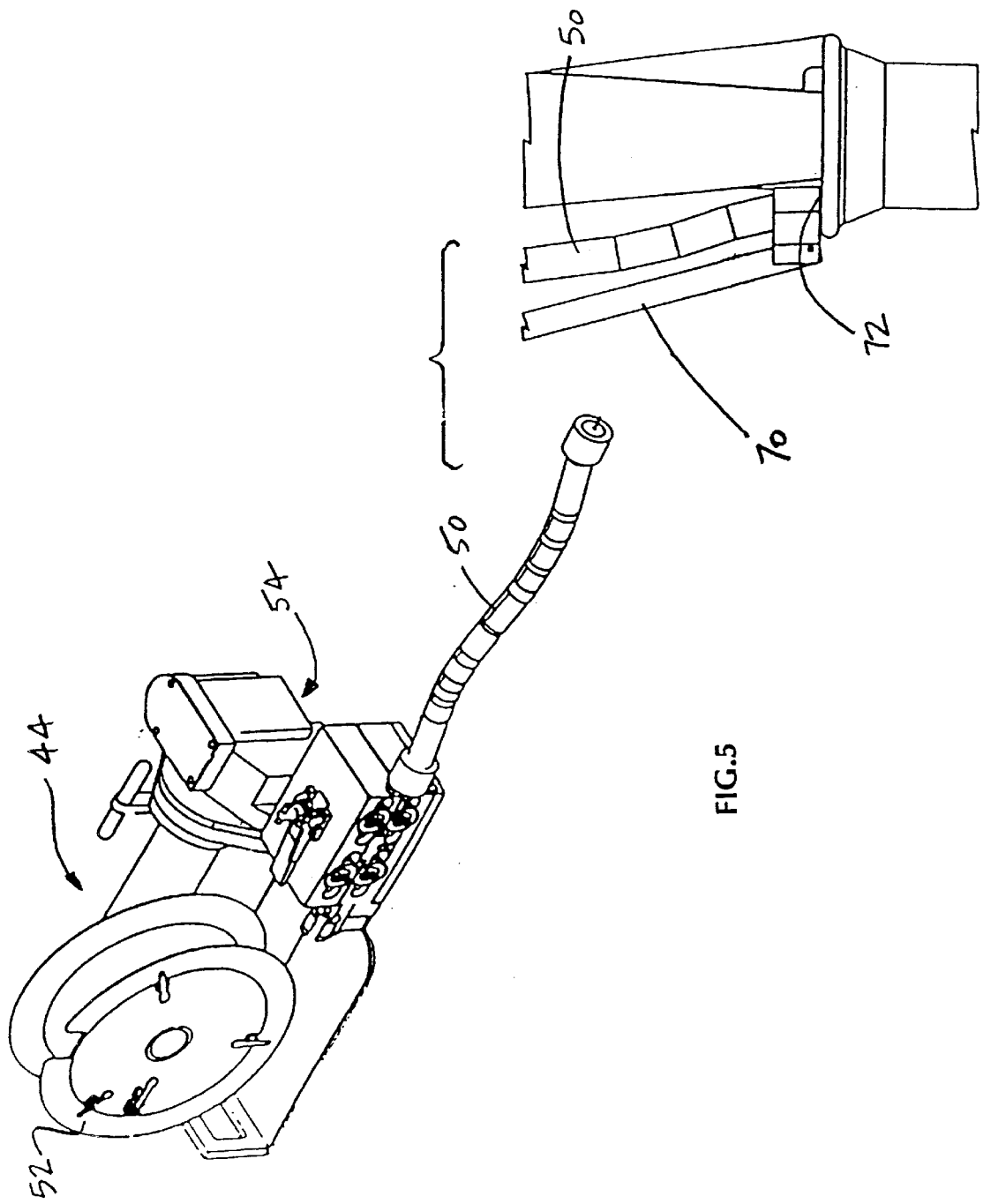
FIG. 5 is a perspective view of the probe driver assembly.

A sheath 50 extends between the probe head 12 and a probe driver assembly 44. The sheath 50 is torsionally rigid yet flexible and acts as a protective shroud for the conductors and pneumatic lines that extend to the probe head. The sheath 50 further functions as the medium for driving the tool axially within the piping. The probe driver assembly 44 is located at the upper-most level of the probe outside the jet pump diffuser to provide for axial movement of the probe along the length of the pipe. The probe driver assembly includes a takeup reel 52 and a set of pinch wheels 54 to lower and raise the probe head along the length of the pipe as illustrated in FIG. 5. In a preferred embodiment, the pinch wheels are driven by a DC servomotor. The probe assembly further includes a means for determining the axial position of the probe within the piping, such as a resolver within an axial encoder. In one embodiment, axial encoding is provided by a separate unit connected to the probe driver and guide tube.

Figure 4:
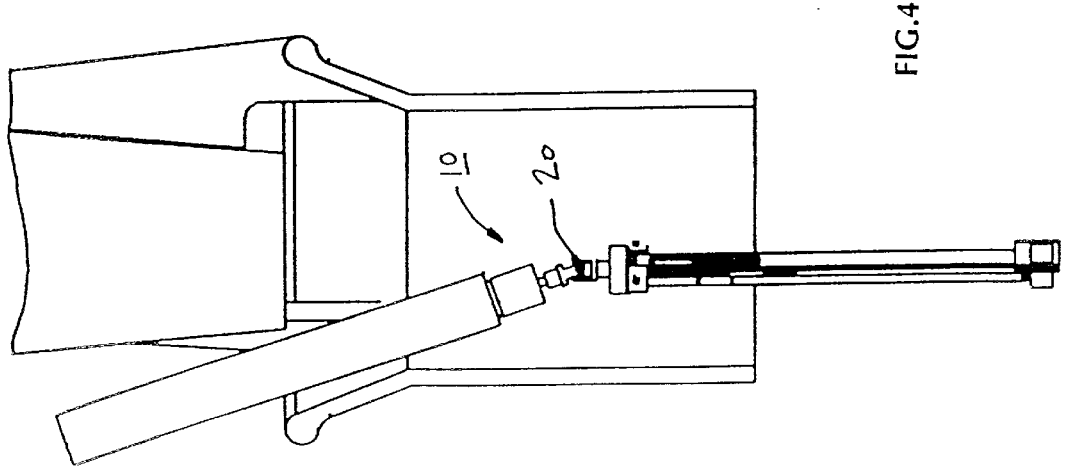
FIG. 4 is a cross-sectional view of the probe being inserted into a pipe.

The flexible joints 20 located along the probe length allow the probe to be bent and manipulated to provide for installation and movement throughout a variety of pipe configurations as illustrated in FIG. 4. In the preferred embodiment, three joints in series, each movable about ±5°, allow the probe housing 12 to be bent sufficiently, over a total range of about 30°, to allow insertion of the probe into the jet pump diffuser. It is understood that the present invention contemplates any number of flexible joints along the probe length depending upon the needs of the hardware being inspected.

The rotational drive motor 22 is positioned within the probe head 12 to rotate the guide arms 16. Preferably, the rotational drive 22 is positioned in proximity to the guide arms 16 to prevent "wind up" which occurs when a length of sheath 50 is rotated causing twist along the sheath length which may cause inaccuracies in the measurements of the inspection. By rotating a short, rigid length of probe, the amount of "wind up" is reduced resulting in greater inspection accuracy. In one preferred embodiment, the rotational drive 22 is a brushless DC motor with Hall-effect commutation for circumferential encoding. In a preferred embodiment, an encoder communicates between the axial and rotational drives to control the speeds of the axial movement of the probe head relative to the rotational movement during the inspection process such that the axial drive is slave to the rotational drive.

A plurality of radially extendable guide arms 16 are placed on the probe head. In a preferred embodiment, three guide arms are spaced about the probe as illustrated in FIG. 1. Each of the guide arms 16 includes an outer arm 24 and a link arm 26. The outer arms 24 are positionable to extend across the inside diameter of a pipe ranging from about 3 to 22 inches and, possibly, having a tapered diameter. The outer arm includes a first end 33 that is pivotally mounted to the probe head and a second end 35 may be equipped with sensor assemblies 32.

A linear actuator 30 including a pneumatic cylinder and the pull rod 51 expands and contracts the guide arms 16 during the inspection process via the link arms 26 that extend between the pull rod 51 and the guide arms. The pull rod 51 is axially pulled and pushed along with the rotational drive 22 by the pneumatic cylinder thereby causing the link arms to push and pull the guide arms opened and closed. By way of example, the guide arms are in a retracted position as illustrated in FIG. 2. To extend the guide arms as illustrated in FIG. 1, the pull rod is axially pulled thereby causing the link arms 26 to push open the guide arms. The pull rod 51 is pulled a greater distance to extend the guide arms to a fully extended position or a lesser amount to extend the guide arms a smaller distance depending upon the inside diameter of the piping. The pneumatic cylinder acts to ensure that the guide arms remain in contact with inner diameter of the piping during the inspection process.

Figure 6:
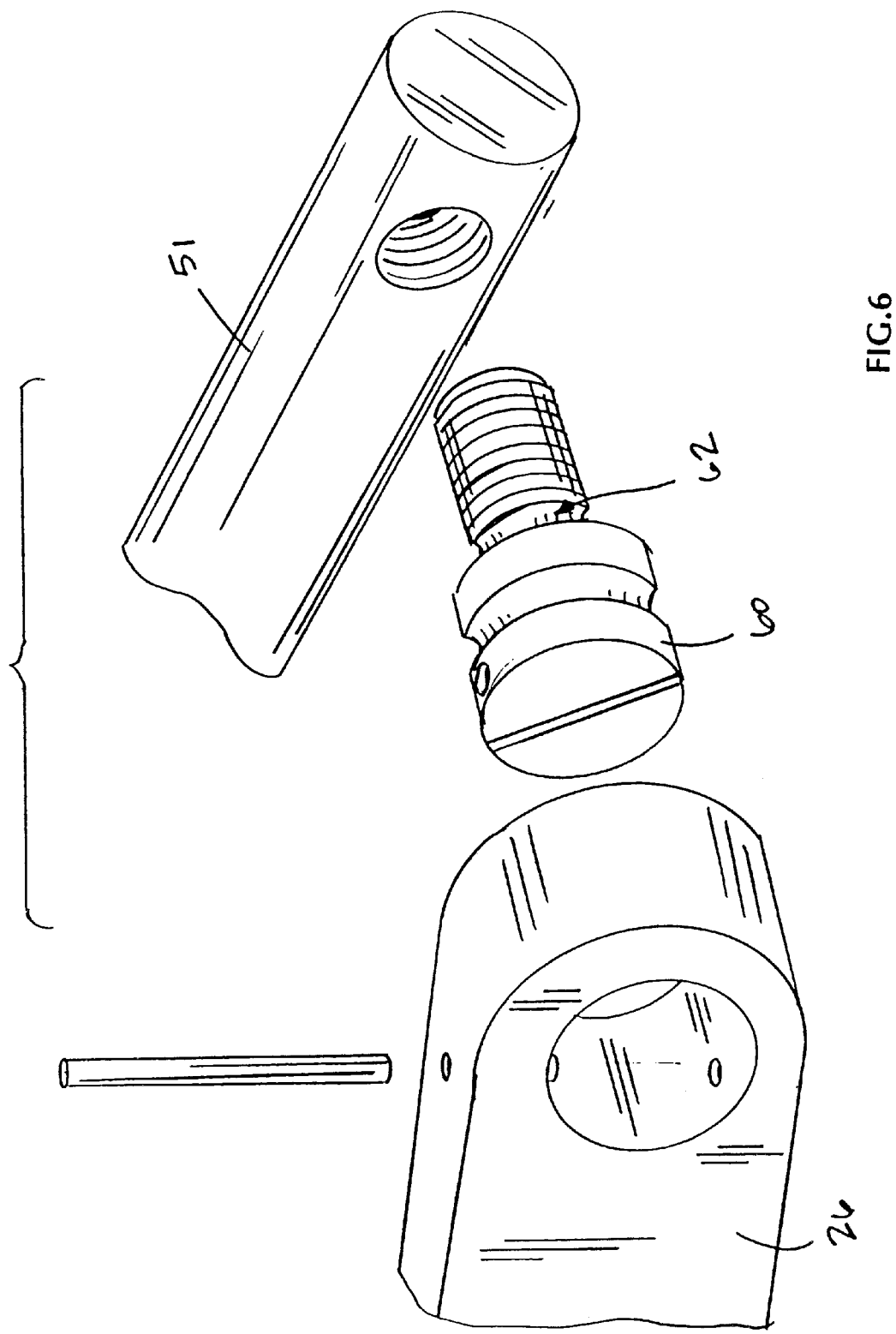
FIG. 6 is an exploded view of the connector attaching the pull rod and link arm.

The link arm 26 is attached to the pull rod 51 by a fastener 60 as illustrated in FIG. 6. The fastener 60 includes a shear plane 62 positioned between the link arm 26 and pull rod 51 such that in the event that the guide arms are stuck in an open position, the force of probe drive 44 pulling the probe head will cause the shear planes to fail, thereby allowing the guide arms to collapse. After the shear plane fails, probe driver assembly 44 axially pulling the probe head out of the piping will cause the guide arms to retract as the guide arms are no longer being kept open. In a preferred embodiment, the angle a between the guide arms 16 and probe head 12 will be about less than or equal to 90 degrees to provide for the axial movement of the probe to close the guide arms. The connection between the guide arms 16 and the pull rod 51 also provides for no particles to break off and escape into the piping as the pieces of the connector are captured.

The sensor assemblies 32 function to detect and length size relevant flaws oriented parallel to the weld and may initiate from either the inner or outer diameter of the piping. The scanning technique involves placement of the sensor assemblies 32 on the inside diameter of the piping and is achieved by pivotally connecting the sensors to the outer arms 24 at pivots 36 as illustrated in FIG. 1.

The sensor assemblies may vary depending upon the specific parameters of the inspection process. In one i embodiment, the sensor assemblies include two circumferential flaw detecting transducers positioned on the first outer arm, one transducer for circumferential flaw detecting on the second outer arm, and two axial flaw detecting transducers on the third outer arm. Preferably, the transducers use 60 degree refracted shear waves directed in both the upward and downward and the clockwise and counter-clockwise directions so that the sound beams are aimed essentially both normal and parallel to the weld axis. In the preferred embodiment, the housing holding the transducers also include small guide wheel that ride on the inside surface of the piping to reduce friction.

A sensor seater 46 is positioned on the probe head to ensure the sensor assemblies 32 are properly seated when the guide arms 16 are retracted as illustrated in FIG. 2. As the guide arms 16 are retracted towards the central axis of the probe head, the sensor assemblies contact the sensor seater 46 causing the sensors to pivot thus allowing them to seat within the probe head.

A weight 14 is positioned downstream of the retracted guide arms position. The weight provides a center of gravity for the probe below the contact point plane of the guide arms where the sensor assemblies contact the inside diameter of the pipe. The weight 14 provides for the probe to maintain central and axial position within the pipe to ensure for more accurate inspection results. Preferably, the weight has a cylindrical shape having less than or about the same diameter of the housing to permit insertion into the same size access openings that the probe body can pass through.

In operation, the guide arms 16 are placed in the full retracted position as illustrated in FIG. 2. The probe is then delivered through a series of handling poles 70 into the piping through the top of the jet pump inlet mixer nozzle 72 as illustrated in FIG. 5. The handling poles 70 provide an in-line calibration standard such that the probe does not have to be removed from the reactor vessel in order to perform a calibration. The flexible joints 20 allow the otherwise rigid probe head 12 to be inserted into the piping. The probe is lowered into the piping weight end 14 first. The probe driver assembly 44 pays out the sheath to allow the probe to descend the proper distance. When the distance is in the correct axial location, the guide arms 16 are extended to allow the sensor assemblies 32 to contact the inside diameter of the piping as illustrated in FIG. 3.

The probe driver assembly 44 moves the probe head 12 through the desired axial length of the piping as the rotational drive 22 rotates the guide arms. The probe moves along the piping length to helically scan the area of interest. When the inspection process is complete, the guide arms are retracted to the closed position, and the probe is pulled from the piping.

It will be understood that the present invention provides for a remotely controlled tool used for the ultrasonic inspection of the welds in a jet pump mixer, diffuser, tail pipe, and adapter of a boiling water reactor. The invention is capable of inspecting all the welds in the adapter, all of the welds in the tail pipe region, all the welds in the diffuser, and some of the welds in the mixer region. It will also be understood that the pitch of the sensor assemblies can be adjusted.

Certain modifications and improvements will occur to those skilled in the art upon a reading of the foregoing description. By way of example, the air cylinder could be a piston within the housing using the rotary drive as the piston body. This would allow greater force to open the guide arms. Also, larger wheels could be incorporated into the transducer housing to further reduce friction. This could be coupled with spring loaded transducers to maintain transducer contact with the pipe wall. Also, the universal joints could be modular to allow further ease in assembly and repair. It should be understood that all such modifications and improvements have been deleted herein for the sake of conciseness and readability but are properly within the scope of the following claims.

We claim:

1. A probe for inspecting the inside of a large diameter, substantially vertical pipe, said probe comprising:
    (a) an elongated probe housing adapted to be positioned within said pipe;
    (b) a plurality of radially extendable guide arms attached adjacent to a distal end of said probe housing for positioning said probe within said pipe; and
    (c) a stabilizer weight vertically suspended from said distal end of said elongated housing for preventing unstable movement of said probe, wherein said stabilizer weight is attached to said elongated housing by a flexible joint.

2. The probe according to claim 1, wherein said stabilizer weight is an elongated cylinder having an outer diameter substantially equal to or less than the diameter of said elongated housing.

3. The probe according to claim 1, wherein each of said guide arms has an outer end and a contact point disposed thereon, and wherein the center of gravity of said weight is below a plane determined by the contact points of the outer ends of the guide arms, thereby maintaining central and axial alignment of said probe.

4. The probe according to claim 1, wherein said flexible joint permits axial bending of about ±5°.

5. The probe according to claim 1, wherein said flexible joint is a universal joint.

6. A probe for inspecting the inside of a large diameter, substantially vertical, limited access pipe, said probe comprising:
    (a) an elongated probe housing having at least one flexible joint to permit said probe to be positioned within said pipe;
    (b) a plurality of radially extendable guide arms attached adjacent to a distal end of said probe housing for positioning said probe within said pipe;
    (c) a stabilizer weight vertically suspended from said distal end of said elongated housing adjacent to said guide arms for preventing unstable movement of said probe, wherein said stabilizer weight is an elongated cylinder having an outer diameter substantially equal to or less than the diameter of said elongated housing; and
    (d) a rotational drive means for rotating said plurality of radially extendable guide arms with respect to said elongated housing and an axial drive means for moving said probe along the length of said pipe, wherein said axial drive means for moving said probe along the length of said pipe is controlled by an output from said means for rotating said plurality of radially extendable guide arms with respect to said elongated housing.

7. A probe for inspecting the inside of a large diameter, substantially vertical, limited access pipe, said probe comprising:
    (a) an elongated probe housing having at least one flexible joint to permit said probe to be positioned within said pipe;
    (b) a plurality of radially extendable guide arms attached adjacent to a distal end of said probe housing for positioning said probe within said pipe, wherein said plurality of radially extendable guide arms each includes an outer arm attached at one end to said probe housing, a linear actuator and a link arm attached to said actuator and said outer arm for extending said guide arms; and (c) a stabilizer weight vertically suspended from said distal end of said elongated housing adjacent to said guide arms for preventing unstable movement of said probe.

8. The probe according to claim 7, wherein at least one of said plurality of radially extendable guide arms includes a sensor assembly for detecting a defect in said pipe.

9. The probe according to claim 8, wherein said sensor assembly is pivotable with respect to the ends of said plurality of guide arms adjacent to the inside surface of said pipe.

10. The probe according to claim 8, wherein said sensor assembly includes an NDE sensor.

11. The probe according to claim 10, wherein said NDE sensor is an ultrasonic crack detector.

12. The probe according to claim 7, wherein said link arms are attached to said linear actuators by shear pins to permit removal of said probe in the event of a failure wherein said plurality of radially extendable guide arms are stuck in an open position.

13. The probe according to claim 12, wherein said shear pins are captured to prevent loose parts in the event of a failure.

14. The probe according to claim 7, wherein each said actuator is a pneumatic cylinder and pull rod.

15. A probe for inspecting the inside of a large diameter, substantially vertical, limited access pipe, said probe comprising:

(a) an elongated probe housing having at least one flexible joint to permit said probe to be positioned within said pipe;

(b) a plurality of radially extendable guide arms attached adjacent to a distal end of said probe housing for positioning said probe within said pipe; and (c) a stabilizer weight vertically suspended from said distal end of said elongated housing adjacent to said guide arms for preventing unstable movement of said probe, wherein said stabilizer weight is attached to said elongated housing by said flexible joint.

16. The probe according to claim 15, wherein each of said guide arms has an outer end and a contact point disposed thereon, and wherein the center of gravity of said weight is below a plane determined by the contact points of the outer ends of the guide arms, thereby maintaining central and axial alignment of said probe.

17. The probe according to claim 15, wherein said flexible joint is a universal joint.

18. The probe according to claim 15, wherein said flexible joint permits axial bending of about ±5°.

19. The probe according to claim 15, wherein said stabilizer weight is an elongated cylinder having an outer diameter substantially equal to or less than the diameter of said elongated housing.

20. The probe according to claim 15, wherein said flexible joint is a universal joint.

21. The probe according to claim 15, wherein said flexible joint permits axial bending of about ±5°.

22. The probe according to claim 15, further including rotational drive means for rotating said plurality of radially extendable guide arms with respect to said elongated housing.

23. The probe according to claim 22, wherein said rotational drive means is located between said elongated housing and said plurality of radially extendable guide arms to reduce wind-up error.

24. The probe according to claim 22, wherein said rotational drive means is a brushless DC servomotor.

25. The probe according to claim 22, further including axial drive means for moving said probe along the length of said pipe.

26. The probe according to claim 25, wherein said axial drive means for moving said probe along the length of said pipe is controlled by an output from said means for rotating said plurality of radially extendable guide arms with respect to said elongated housing.

27. The probe according to claim 15, wherein said plurality of radially extendable guide arms attached to the lower end of said probe housing for positioning said probe within said pipe each includes an outer arm attached at one end to said probe housing, a linear actuator and a link arm attached to said actuator and said outer arm for extending said guide arms.

28. The probe according to claim 27, wherein at least one of said plurality of radially extendable guide arms includes a sensor assembly for detecting a defect in said pipe.

29. The probe according to claim 28, wherein said sensor assembly is pivotable with respect to the end of said at least on of said plurality of guide arms adjacent to the inside surface of said pipe.

30. The probe according to claim 28, wherein said sensor assembly includes an NDE sensor.

31. The probe according to claim 30, wherein said NDE sensor is an ultrasonic crack detector.

32. The probe according to claim 27, wherein said link arms are attached to said linear actuators by shear pins to permit removal of said probe in the event of a failure wherein said plurality of radially extendable guide arms are stuck in an open position.

33. The probe according to claim 32, wherein said shear pins are captured to prevent loose parts in the event of a failure.

34. The probe according to claim 27, wherein each said actuator is a pneumatic cylinder and pull rod.

* * * * *